United States Patent [19]
Leight

[11] Patent Number: 5,811,742
[45] Date of Patent: Sep. 22, 1998

[54] DUAL EARPLUG

[75] Inventor: Howard S. Leight, San Diego, Calif.

[73] Assignee: Howard S. Leight and Associates, Inc., San Diego, Calif.

[21] Appl. No.: 944,094

[22] Filed: Oct. 2, 1997

Related U.S. Application Data

[60] Provisional application No. 60/043,733 Apr. 21, 1997.

[51] Int. Cl.$^6$ .............................. A61B 7/02; A61F 11/00
[52] U.S. Cl. ........................................... 181/135; 128/864
[58] Field of Search .................................. 181/130, 135; 128/864, 865, 867

[56] References Cited

U.S. PATENT DOCUMENTS

| | | |
|---|---|---|
| 2,538,339 | 1/1951 | Thomas . |
| 3,618,600 | 11/1971 | Douglass . |
| 3,736,929 | 6/1973 | Mills . |
| 4,143,657 | 3/1979 | Takeda . |
| 4,384,575 | 5/1983 | Asker . |
| 4,579,112 | 4/1986 | Scott . |
| 5,483,027 | 1/1996 | Krause ................................. 181/135 |
| 5,573,015 | 11/1996 | Williams ............................. 128/864 |

*Primary Examiner*—Khanh Dang
*Attorney, Agent, or Firm*—Freilich Hornbaker Rosen

[57] ABSTRACT

An elongated earplug of slow recovery material has one end portion (14) for use in large ear canals to effectively block noise therein and an opposite end portion (16) for use in small diameter ear canals to block noise while maintaining a moderate comfort level for the wearer. The opposite end portions of the earplug are of different colors, to enable a person picking up the earplug to quickly determine which end to place in the ear as well as to identify the earplug as a dual type. The larger end is preferably of a lighter color such as yellow, then the darker end which is of a darker color such as medium to dark green or orange, to emphasize the largeness of the large end and the smallness of the small end. One dual earplug has a small end portion which is tapered along most of its length, at an included tapered angle (B) of about 15°, with the end portion progressively increasing in diameter until merges with the large end, without a step in diameters thereat, which facilitates rolling of slow recovery material in the fingers prior to insertion.

5 Claims, 2 Drawing Sheets

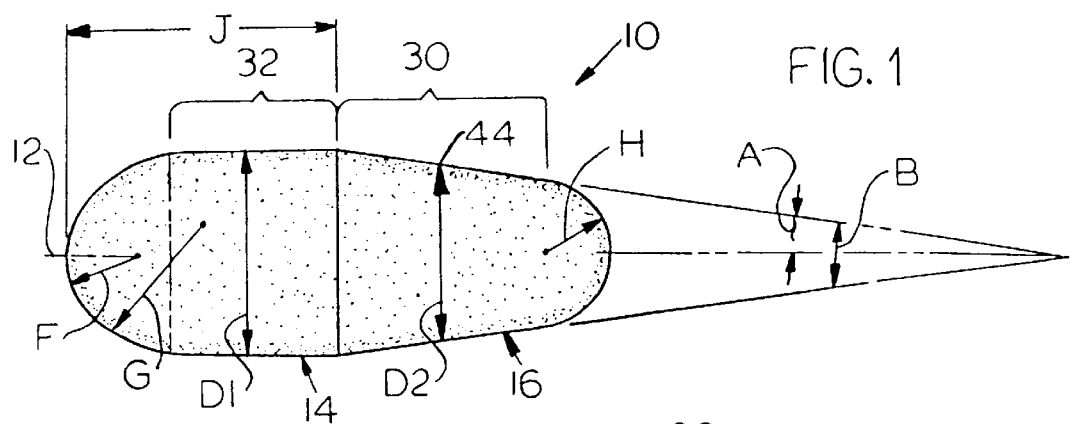
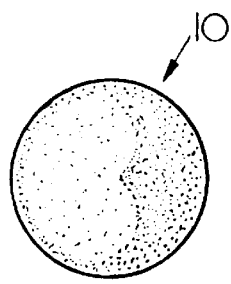
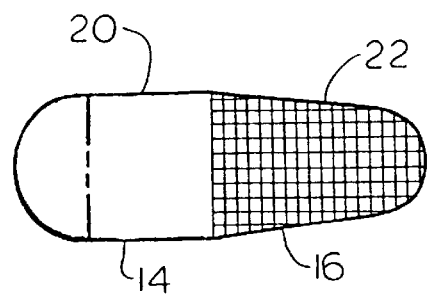
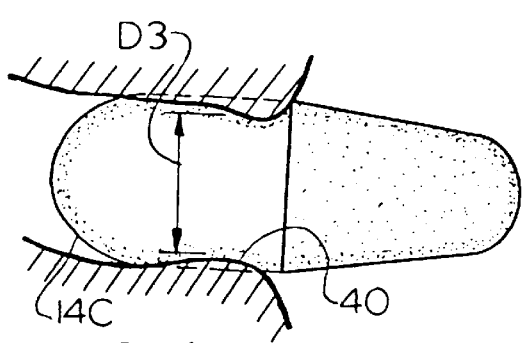
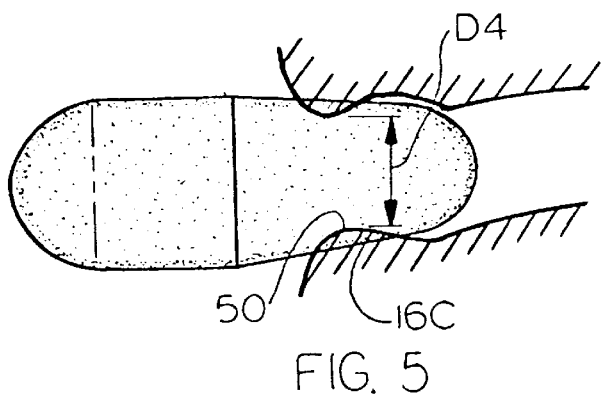
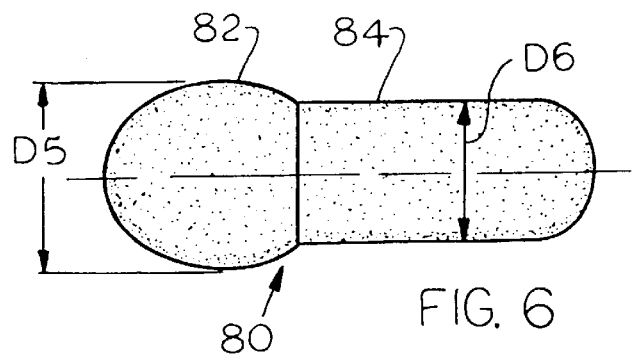

DUAL EARPLUG

CROSS REFERENCE TO RELATED APPLICATION

This application claims the benefit of U.S. provisional application No. 06/043,733 filed on Apr. 21, 1997.

BACKGROUND OF THE INVENTION

Earplugs of slow recovery material, such as is described in U.S. Pat. No. 4,774,938, are used in large numbers in industries where workers' ears must be protected from loud noises. Workers take pairs of earplugs from large containers once to a few times a day, and dispose of the pair after using them. The earplugs have a front portion for entering the ear canal, with the front portion having a diameter of about 0.40 inch, which blocks the ear canals of a great majority of workers although with varying degrees of comfort. A significant number of workers with smaller ear canals experience some discomfort because the earplug, when expanded, presses with more force than necessary to block noise. Such workers may insert the earplug to a shallower depth within the ear canal to avoid discomfort, and the earplug then may not block noise as effectively as when fully inserted. For some workers with large diameter ear canals, the earplugs are not always highly effective in blocking noise, which could lead to damage to the workers hearing. Such workers can attempt to block noise by inserting the ear canal slightly deeper than usual, but this still may not effectively block noise.

It would be possible to provide earplugs of different sizes, so workers could choose the earplug most appropriate to him/her. However, this necessitates keeping an inventory of two different sizes, which can add expense and complication. For example, many factories purchase a dispenser that a worker can operate to dispense two earplugs without any worker touching the batch of earplugs with possibly dirty hands. If two different sizes of earplugs are to be provided, then two dispensers would be required, adding to cost and space requirements.

It is possible to form a single earplug with opposite ends of different diameters for fitting into ear canals of different diameters. U.S. Pat. No. 4,384,575 shows an elastic gas-filled shell in the shape of an elongated football with slightly different taperings at its opposite ends for fitting into ear canals of different sizes. It could be difficult for a person viewing such an earplug to determine which end is the smaller or larger one. A single low cost earplug which could effectively and comfortably fit into ear canals of different sizes, where each end could be easily identified and where an earplug of slow recovery material could be easily rolled to a small diameter for insertion, would be of value.

SUMMARY OF THE INVENTION

In accordance with one embodiment of the present invention, applicant provides a single earplug for comfortably and effectively blocking of ear canals of different canal sizes, which enables easy identification of which end to insert into a particular person's ear canal, and which enables an earplug of slow recovery material to be easily rolled prior to insertion. The earplug has an elongated shape with first and second opposite end portions of different diameters, with each end portion having a different color to enable a person to determine which end to insert by a simple glance at the earplug. The larger end is preferably of the lighter color, while the smaller end is of a darker color, to emphasize the larger and smaller sizes.

The earplug can be formed of slow recovery material with the small end being tapered at a small constant included angle of about 15° along most of its length. The small end portion merges with the large end portion without a step that would hamper rolling of slow recovery material prior to insertion in the ear canal. The large diameter end preferably has a portion that is cylindrical rather than tapered, to more easily identify the large diameter end and to facilitate its molding.

The novel features of the invention are set forth with particularity in the appended claims. The invention will be best understood from the following description when read in conjunction with the accompanying drawings.

BRIEF DESCRIPTION OF THE DRAWINGS

FIG. 1 is a side elevation view of a dual earplug constructed in accordance with one embodiment of the present invention.

FIG. 2 is a view of one end of the earplug of FIG. 1.

FIG. 3 is a view similar to that of FIG. 1, but with the colors of the opposite ends being shown by color cross hatching.

FIG. 4 is a side elevation view of the earplug of FIG. 1, showing the larger end fully installed in a larger ear canal.

FIG. 5 is a side elevation view of the earplug of FIG. 1, showing the smaller end fully installed in a smaller ear canal.

FIG. 6 is a side elevation view of a dual earplug constructed in accordance with another embodiment of the invention.

DESCRIPTION OF THE PREFERRED EMBODIMENTS

Figure 7:
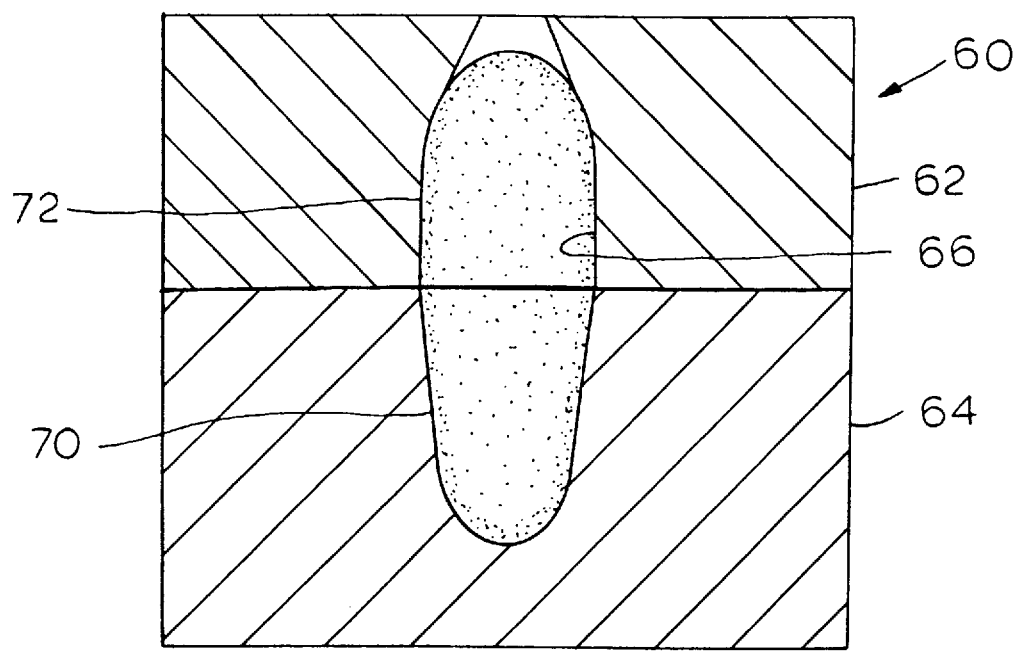
FIG. 7 is a side view of a mold for forming a dual earplug.

FIG. 1 illustrates an earplug that is elongated along an axis 12 and symmetrical about the axis. The earplug has first and second opposite end portions 14, 16, that are each designed to lie in an interference fit in an ear canal to block the passage of noise through the ear canal. The first end portion has a large diameter D1 at a location where it is designed to enter an ear canal, while the second end portion has a smaller diameter D2 at a location that is designed to enter the ear canal and lie at the ear canal entrance. The earplug is substantially filled with slow recovery material, so there are no air gaps or insert except, for example, a small metal insert (volume not more than 15% and preferably not more than 10% of total earplug volume) for detecting an earplug that has fallen into a batch of food, or the like.

FIG. 3 shows the earplug of FIG. 1, but with lines showing the different colors 20, 22 of the different end portions 14, 16. The different colors allow a person to determine which end of the earplug is a larger one, at a glance and even in poor lighting conditions. In FIG. 3, the color 20 of the larger end portion is a light coral, while the color 22 of the second end portion is of a dark yellow. A lighter color tends to make an object appear larger, while a darker color tends to make an object appear smaller. Thus, the lighter color for the large end portion 14 emphasizes its larger size while the darker color for the second end portion emphasizes its smaller size.

The second or smaller end portion 16 (FIG. 1) of the earplug is tapered along its entire length, with the tapering along the length 30 which is most of the length and actually all of it except the small end that does not block the ear canal, being at a constant taper angle A of about 7½ degrees from the axis 12 and forming an included angle B of 15°. For a medium to high friction material such as a molded slow recovery foam, the friction of the earplug surface with the ear canal avoids the earplug working its way out of the ear canal for a small taper angle B of about 15°. The large end portion 14 is cylindrical at a part 32 that is about half or more of the length of the end portion 14. The presence of the cylinder at 32 helps to visually distinguish the large end from the small end which is tapered along its entire length. The tapering of the small end portion 16 results in it merging with the cylinder at 32, which avoids steps. By avoiding steps, applicant provides a continuous variation in diameter from small to large, to more comfortably fit a person with a medium size ear canal. Also, avoiding steps makes it somewhat easier to roll the slow recovery material into a small diameter for insertion into the ear canal.

FIGS. 4 and 5 show the opposite end portions of the earplug installed into ear canals of different sizes. In FIG. 4, the large end 14C of the earplug is shown having been installed through the larger-than-usual entrance 40 to a large ear canal 42. The larger earplug end portion 14 has an uncompressed diameter D1 of about 0.43 inch, while the larger-than-usual entrance 40 to the particular person's ear canal shown in FIG. 4, has a diameter D3 of 0.33 inch. As a result, the large diameter end portion at 14C is compressed by about 24% at the entrance 40 and somewhat less at larger diameter portions of the ear canal. The small diameter end 16 (FIG. 1) of the earplug has a diameter D2 of about 0.37 inch at a location 44 halfway along its region 30 of constant taper. If only the small diameter end portion 16 were inserted into the large ear canal entrance 20 (of 0.33 inch diameter), then there would be minimal (less than 15%) compression at the entrance 40 and likely no compression at larger diameter portions of the large ear canal, resulting in less than highly effective noise blocking. It is noted that the entrance to the ear canal is often non-circular so only slight earplug compression can leave a gap.

In FIG. 5, the entrance 50 to the small ear canal has a diameter D4 of about 0.27 inch. This results in the small diameter earplug end portion at the location 44, being compressed to the configuration 16C wherein it is compressed by about 27% at the entrance to the ear canal. Such compression is generally effective and comfortable. If the large diameter end portion 14 of the earplug were inserted into the smaller ear canal, then at the entrance 50, the compression of the earplug would be 37%, which is likely to be uncomfortable to the person who has the smaller diameter ear canal.

To form the earplug 10, a quantity of flowable slow recovery material of a particular color is deposited in a first portion of a cavity that has the shape of the earplug. Another quantity of flowable slow recovery material of a different color is deposited in another portion of the cavity. The tapered ends of the finished earplugs easily come out of the mold, to facilitate earplug removal. FIG. 7 shows a mold 60 with two mold parts 62, 64 that form a cavity 66 between them. First, a quantify 70 of flowable slow recovery material of a first color is deposited in the cavity. Then, a second quantity 72 of slow recovery material of a different second color is deposited in the cavity. When the materials are foamed and set, they can be removed from the cavity, the tapered end facilitating removal from the cavity part 64. The second quantity 72 of material can be deposited before or after the first quantity has set, waiting for the first quantity to foam and largely set has the advantage of minimizing the running of one color into the other. The earplugs can be molded by injection molding in a closed mold, with the "depositing" accruing by injecting.

To use the earplug 10 of FIG. 1, a person takes two earplugs and rolls them one at a time between his fingers and inserts the rolled earplug into his ear. A factory worker may try the different ends in his ear and will know which end he wants to place in his ear canal. The distinctly different colors at the opposite end portions of the earplug make it easy for the person to determine which end to insert even when the earplug has been rolled to a small diameter along its entire length. Even in a dark or poorly illuminated environment, the person can tell where the originally cylindrical portion 33 lay by its greater resistance to rolling then the smaller diameter end portion. The fact that there are no sudden changes in earplug diameter or steps, facilitates rolling the earplug. As with all slow recovery earplugs, an end portion of the earplug inserted into a person's ear canal, is kept there for perhaps one-half minute, until it has expanded and retains itself in place. The depth of insertion of the tapered smaller end portion can be adjusted for greater comfort and effective noise blocking, while assuring retention because of the constant taper angle B of about 15° (10° to 23° and preferably 10° to 20°).

In an earplug of the construction shown in FIG. 3 that applicant has designed, the earplug had an overall length of 1.23 inch. The tip of the large end portion had radii of curvatures indicated by F and G of 0.15 and 0.29 inch respectively. The small diameter end had a radius H of 0.15 inch and a diameter of about 0.30 inch which is about ⅔rds of the maximum diameter D1 of the earplug. The large diameter end had a length J of 0.60 inch, and had a length of 0.34 inch along the cylindrical region 32. The small diameter end portion had a length along the constant taper 30 of 0.47 inch. The diameters D1 and D2 were 0.43 inch and 0.38 inch. The other dimensions are relative to those mentioned above, as illustrated in FIG. 1.

FIG. 6 shows another dual earplug 80 that applicant has designed, wherein the large diameter end portion 82 was of largely spherical shape with slight elongation, while the smaller end portion 84 was cylindrical. The large diameter end had a diameter D5 of 0.43 inch while the small diameter end had a diameter D6 of 0.37 inch. The opposite end portions were of different colors, such as the yellow and green colors.

Thus, the invention provides a dual earplug for blocking noise, which has different effective diameters at its opposite end portions for comfortably and effectively blocking the ear canals of persons with ear canals of different sizes. The different ends are preferably of different colors to enable a person to easily determine which end best fits in his/her ear. The smaller end is preferably of a darker color to emphasize the different sizes, although this is not necessarily so. In a preferred design, the smaller end portion is tapered at a constant taper angle of about 15° along most of its length, while the larger end portion has a cylindrical part, and with the end portions merging without any step or sudden change in earplug diameter. This design enables easy identification of the different ends and enables easy molding of the earplug. It is possible to provide an earplug where the opposite ends are of the same diameter, as where the opposite ends are cylinders of the same diameters.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A dual ended earplug, comprising:

a quantity of elastomeric material having an elongated shape with first and second opposite end portions, wherein each of said end portions is formed to lie in an interference fit in an ear canal and block the passage of noise through the ear canal, with said first end portion being of a larger end portion diameter to comfortably and efficiently block an ear canal of a first larger canal diameter, and said second end being of a smaller end portion diameter that is smaller than said larger end portion diameter to comfortably and efficiently block an ear canal of a second smaller canal diameter which is smaller than said first larger canal diameter;

said first end portion having a first color and said second end portion having a second color which is distinctly different than said first color, with the first and second colors together covering the entire surface of the earplug.

2. The dual ended earplug described in claim 1 wherein:

said first color being lighter than said second color, to emphasize the largeness of said first end portion and the smallness of said second end portion.

3. The dual ended earplug described in claim 1 wherein:

said elastomeric material is a slow recovery foam material which occupies substantially the entire volume of said earplug;

said second end portion of said earplug is tapered to have a progressively greater diameter at locations progressively closer to said first end portion, and said second end portion merges with said first end portion without an abrupt change in diameter, and said first end portion has a cylindrical part and a rounded first end, whereby to aid in molding and identification.

4. A method for forming a dual ended earplug, comprising:

depositing a first quantity of flowable and setable elastomeric material in a mold cavity that defines an earplug, where said first quantity has a first color;

depositing a second quantity of flowable and setable elastomeric material in said mold cavity, where said second quantity has a second color that is different from said first color;

allowing said quantities to set and bond to each other, and removing them from said mold.

5. The method described in claim 4 wherein:

said steps of depositing includes depositing foamable material, and said step of depositing a second quantity includes depositing said second quantity only after said first quantity has foamed and primarily set, to minimize running of one material into another.

* * * * *